United States Patent
Crone et al.

(10) Patent No.: US 7,417,173 B2
(45) Date of Patent: Aug. 26, 2008

(54) METHOD FOR PRODUCING BUTADIENE FROM N-BUTANE

(75) Inventors: Sven Crone, Limburgerhof (DE);
Catharina Klanner, Mannheim (DE);
Götz-Peter Schindler, Mannheim (DE);
Mark Duda, Ludwigshafen (DE);
Frieder Borgmeier, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 15 days.

(21) Appl. No.: 11/718,814

(22) PCT Filed: Nov. 11, 2005

(86) PCT No.: PCT/EP2005/012109
§ 371 (c)(1),
(2), (4) Date: May 8, 2007

(87) PCT Pub. No.: WO2006/050969
PCT Pub. Date: May 18, 2006

(65) Prior Publication Data
US 2007/0244349 A1 Oct. 18, 2007

(30) Foreign Application Priority Data
Nov. 12, 2004 (DE) ........................ 10 2004 054 766

(51) Int. Cl.
*C07C 5/333* (2006.01)
(52) U.S. Cl. ........................ 585/325; 585/616; 585/621; 585/628; 585/629
(58) Field of Classification Search .................. 585/325, 585/616, 621, 628, 629
See application file for complete search history.

(56) References Cited
U.S. PATENT DOCUMENTS
3,161,670 A * 12/1964 Adams et al. ................ 558/320
(Continued)

FOREIGN PATENT DOCUMENTS
WO WO-2004/007408 1/2004

*Primary Examiner*—Thuan Dinh Dang
(74) *Attorney, Agent, or Firm*—Connolly Bove Lodge & Hutz LLP

(57) ABSTRACT

Processes for producing butadiene from n-butane comprising: (a) providing a feed gas stream comprising n-butane; (b) non-oxidatively dehydrogenating the feed gas stream in the presence of a catalyst in a first dehydrogenation zone to form a first intermediate gas stream comprising n-butane, 1-butene, 2-butene, butadiene and hydrogen; (c) oxidatively dehydrogenating the first intermediate gas stream in the presence of an oxygenous gas having an oxygen content of at least 75% by volume in a second dehydrogenation zone to form a second intermediate gas stream comprising n-butane, butadiene, hydrogen, carbon dioxide and steam; (d) compressing and cooling the second intermediate gas to form a first condensate stream comprising water and a third intermediate gas stream comprising n-butane, butadiene, hydrogen, carbon dioxide and steam; (e) compressing and cooling the third intermediate gas to form a second condensate stream comprising n-butane, butadiene and water and a fourth intermediate gas stream comprising n-butane, butadiene, hydrogen and carbon dioxide; (1) cooling the fourth intermediate gas stream to form a third condensate stream comprising n-butane and butadiene, and an offgas stream comprising carbon dioxide and hydrogen; (g) removing water from the second condensate stream and combining the second condensate stream and third condensate stream to form a $C_4$ hydrocarbon stream comprising n-butane and butadiene; and (h) separating the $C_4$ hydrocarbon stream to form a recylce stream comprising n-butane and a product stream comprising butadiene; wherein at least a portion of the recycle stream is fed to the first dehydrogenation zone.

13 Claims, 1 Drawing Sheet

U.S. PATENT DOCUMENTS 4,595,788 A    6/1986  Yamamoto et al.
4,718,986 A    1/1988  Comiotto et al.

2005/0171311 A1    8/2005  Schindler et al.

* cited by examiner

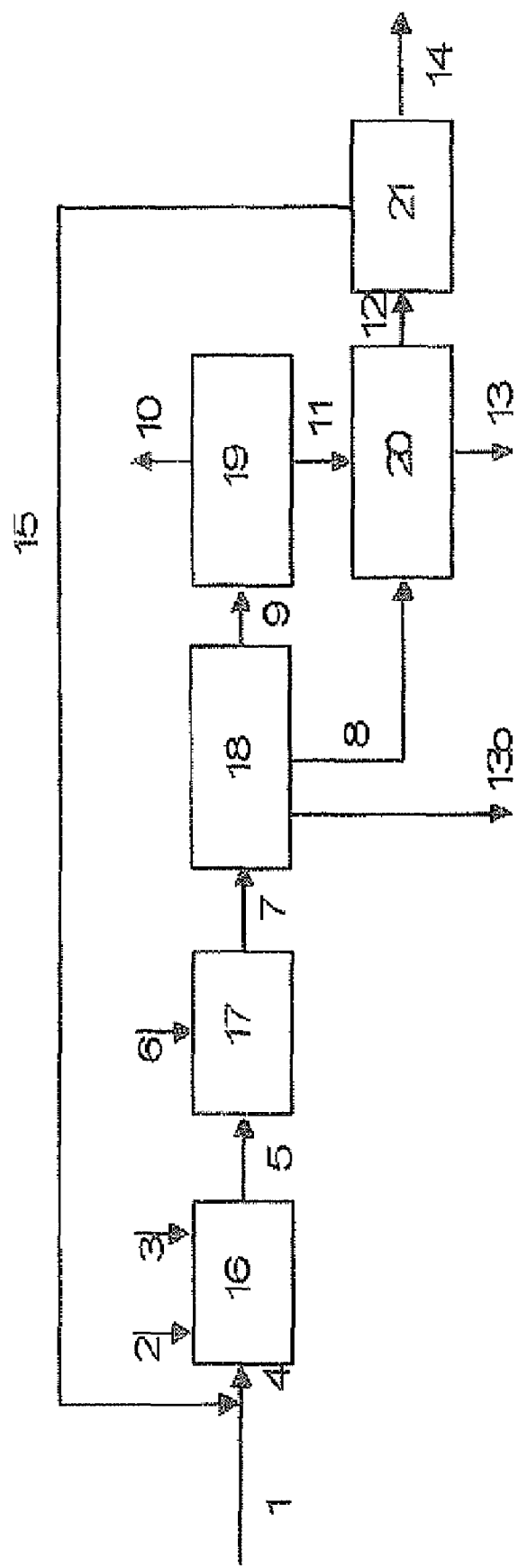

METHOD FOR PRODUCING BUTADIENE FROM N-BUTANE

CROSS-REFERENCE TO RELATED APPLICATIONS

This application is a national stage application, under 35 U.S.C. §371, of PCT/EP2005/012109, filed Nov. 11, 2005, which claims priority of German Application No. 10 2004 054 766.1, filed Nov. 12, 2004.

BACKGROUND OF THE INVENTION

The invention relates to a process for preparing butadiene from n-butane.

BRIEF DESCRIPTION OF DRAWING(S)

The FIGURE is a block diagram of one embodiment of the process.

Butadiene is an important basic chemical and is used, for example, to prepare synthetic rubbers (butadiene homopolymers, styrene-butadiene-rubber or nitrile rubber) or for preparing thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Dimerization of butadiene also allows vinylcyclohexene to be generated, which can be dehydrogenated to styrene.

Butadiene can be prepared by thermally cracking (steamcracking) saturated hydrocarbons, in which case naphtha is typically used as the raw material. In the steamcracking of naphtha, a hydrocarbon mixture of methane, ethane, ethene, acetylene, propane, propene, propyne, allene, butenes, butadiene, butynes, methylallene, $C_5$ and higher hydrocarbons is obtained.

A disadvantage of the generation of butadiene in a cracking process is that larger amounts of undesired coproducts are inevitably obtained.

BRIEF SUMMARY OF THE INVENTION

It is an object of the invention to provide a process for preparing butadiene from n-butane, in which coproducts are obtained to a minimal extent.

The object is achieved by a process for preparing butadiene from n-butane, comprising the steps of A) providing a feed gas stream a comprising n-butane;
B) feeding the feed gas stream a comprising n-butane into at least one first dehydrogenation zone and nonoxidatively, catalytically dehydrogenating n-butane to obtain a gas stream b comprising n-butane, 1-butene, 2-butene, butadiene and hydrogen, with or without carbon dioxide and with or without steam;
C) feeding the gas stream b and an oxygenous gas into at least one second dehydrogenation zone and oxidatively dehydrogenating 1-butene and 2-butene to obtain a gas stream c comprising n-butane, butadiene, hydrogen, carbon dioxide and steam,
D) compressing in at least one first compression stage and cooling the gas stream c to obtain at least one condensate stream d1 comprising water and a gas stream d2 comprising n-butane, butadiene, hydrogen, carbon dioxide and steam,
E) compressing in at least one further compression stage and cooling the gas stream d2 to obtain at least one condensate stream e1 comprising n-butane, butadiene and water, and a gas stream e2 comprising n-butane, butadiene, hydrogen and carbon dioxide,
F) cooling the product gas stream e2 to obtain a condensate stream f1 comprising n-butane and butadiene, and an offgas stream f2 comprising carbon dioxide and hydrogen,
G) removing water from the at least one condensate stream e1 and, if appropriate, from the condensate stream f1 by phase separation to obtain a $C_4$ hydrocarbon stream g1 comprising n-butane and butadiene, and at least one wastewater stream g2.
H) separating the $C_4$ hydrocarbon stream g1 into a recycle stream h1 comprising n-butane and a product stream h2 consisting substantially of butadiene, and recycling the stream h1 into the first dehydrogenation zone.

The process according to the invention is notable for particularly effective utilization of the raw materials. Thus, losses of the n-butane raw material are minimized by recycling unconverted n-butane into the dehydrogenation. The coupling of nonoxidative catalytic dehydrogenation and oxidative dehydrogenation achieves a high butadiene yield. Compared to the generation of butadiene by cracking, the process is notable for high selectivity. No coproducts are obtained.

The complicated removal of butadiene from the product gas mixture of the cracking process is dispensed with.

DETAILED DESCRIPTION OF THE INVENTION

In a first process part, A, a feed gas stream a comprising n-butane is provided. Typically, the starting raw materials are n-butane-rich gas mixtures such as liquefied petroleum gas (LPG). LPG comprises substantially saturated $C_2$-$C_5$ hydrocarbons. In addition, it also comprises methane and traces of $C_6^+$ hydrocarbons. The composition of LPG can vary markedly. Advantageously, the LPG used contains at least 10% by weight of butanes.

Alternatively, a refined $C_4$ stream from crackers or refineries may be used.

In one variant of the process according to the invention, the provision of the dehydrogenation feed gas stream comprising n-butane comprises the steps of (A1) providing a liquefied petroleum gas (LPG) stream,
(A2) removing propane and any methane, ethane and $C_5^+$ hydrocarbons (mainly pentanes, additionally hexanes, heptanes, benzene, toluene) from the LPG stream to obtain a stream comprising butanes (n-butane and isobutane),
(A3) removing isobutane from the stream comprising butanes to obtain the feed gas stream comprising n-butane, and, if desired, isomerizing the isobutane removed to give an n-butane/isobutane mixture and recycling the n-butane/isobutane mixture into the isobutane removal.

Propane and any methane, ethane and $C_5^+$ hydrocarbons are removed, for example, in one or more customary rectification columns. For example, in a first column, low boilers (methane, ethane, propane) may be removed overhead, and, in a second column, high boilers ($C_5^+$ hydrocarbons) may be removed at the bottom of the column. A stream comprising butanes (n-butane and isobutane) is obtained, from which isobutane is removed, for example in a customary rectification column. The remaining stream comprising n-butane is used as the feed gas stream for the downstream butane dehydrogenation.

The isobutane stream removed can be subjected to an isomerization. To this end, the stream comprising isobutane is fed into an isomerization reactor. The isomerization of isobutane to n-butane may be carried out as described in GB-A 2 018 815. An n-butane/isobutane mixture is obtained and is fed into the n-butane/isobutane separating column.

The isobutane stream removed may also be sent to a further use, for example for preparing methacrylic acid, polyisobutene or methyl tert-butyl ether.

The feed gas stream a, comprising n-butane, comprises generally at least 60% by weight of n-butane, preferably at least 90% by weight of n-butane. In addition, it may also comprise $C_1$-$C_6$ hydrocarbons as secondary constituents.

In one process part, B, the feed gas stream comprising n-butane is fed into a dehydrogenation zone and subjected to a nonoxidative catalytic dehydrogenation. In this dehydrogenation, n-butane is partly dehydrogenated in a dehydrogenation reactor over a dehydrogenating catalyst to give 1-butene and 2-butene, and butadiene is also formed. In addition, hydrogen and small amounts of methane, ethane, ethene, propane and propene are obtained. Depending on the method of the dehydrogenation, carbon dioxides (CO, $CO_2$), water and nitrogen may also be present in the product gas mixture of the nonoxidative catalytic n-butane dehydrogenation. Unconverted n-butane is additionally present in the product gas mixture.

The nonoxidative catalytic n-butane dehydrogenation may be carried out with or without oxygenous gas as a cofeed. It is preferably carried out as an autothermal nonoxidative catalytic dehydrogenation with feeding of oxygen as a cofeed. In the autothermal method, the heat required is generated directly in the reactor system by combustion of hydrogen and/or hydrocarbons in the presence of oxygen. If appropriate, a cofeed comprising hydrogen may additionally be admixed. Oxygen may also be fed in as pure oxygen or as oxygenous gas, although the oxygen content is at least 75% by volume, preferably at least 90% by volume. A suitable oxygenous gas is oxygen of technical grade purity, having an oxygen content of approx. 99% by volume. As a result of the use of an oxygenous cofeed with a high oxygen content, only small amounts of inert gases (nitrogen) are introduced into the overall process. This allows the $C_4$ hydrocarbons to be separated from hydrogen and carbon dioxide readily by condensing out the $C_4$ hydrocarbons. Owing to the low inert gas content in the gas stream e2, the loss of $C_4$ hydrocarbons in the condensation step F) remains at a minimum.

One feature of the nonoxidative method compared to an oxidative method is that free hydrogen is not formed in substantial amounts in the oxidative dehydrogenation.

The nonoxidative catalytic n-butane dehydrogenation may in principle be carried out in any reactor types and methods disclosed by the prior art. A comparatively comprehensive description of dehydrogenation processes suitable in accordance with the invention is also contained in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

A suitable reactor form is a fixed bed tubular or tube bundle reactor. In these reactors, the catalyst (dehydrogenation catalyst and, when working with oxygen as the cofeed, optionally a specialized oxidation catalyst) is disposed as a fixed bed in a reaction tube or in a bundle of reaction tubes. The reaction tubes are customarily heated indirectly by the combustion of a gas, for example a hydrocarbon such as methane, in the space surrounding the reaction tubes. It is favorable to apply this indirect form of heating only to about the first 20 to 30% of the length of the fixed bed and to heat the remaining bed length to the required reaction temperature by the radiant heat released in the course of indirect heating. Customary reaction tube internal diameters are from about 10 to 15 cm. A typical dehydrogenation tube bundle reactor comprises from about 300 to 1000 reaction tubes. The internal temperature in the reaction tubes typically varies in the range from 300 to 1200° C., preferably in the range from 500 to 1000° C. The working pressure is customarily from 0.5 to 8 bar, frequently from 1 to 2 bar, when a small steam dilution is used (analogously to the Linde process for propane dehydrogenation), or else from 3 to 8 bar when a high steam dilution is used (analogously to the steam active reforming process (STAR process) for dehydrogenating propane or butane of Phillips Petroleum Co., see U.S. Pat. No. 4,902,849, U.S. Pat. No. 4,996,387 and U.S. Pat. No. 5,389,342). Typical gas hourly space velocities (GHSV) are from 500 to 2000 $h^{-1}$, based on the hydrocarbon used. The catalyst geometry may, for example, be spherical or cylindrical (hollow or solid).

The nonoxidative catalytic n-butane dehydrogenation may also be carried out under heterogeneous catalysis in a fluidized bed, as described in Chem. Eng. Sci. 1992 b, 47 (9-11) 2313. Appropriately, two fluidized beds are operated in parallel, of which one is generally in the state of regeneration. The working pressure is typically from 1 to 2 bar, the dehydrogenation temperature generally from 550 to 600° C., The heat required for the dehydrogenation is introduced into the reaction system by preheating the dehydrogenation catalyst to the reaction temperature. The admixing of a cofeed comprising oxygen allows the preheater to be dispensed with and the required heat to be generated directly in the reactor system by combustion of hydrogen and/or hydrocarbons in the presence of oxygen. If appropriate, a hydrogen-containing cofeed may additionally be admixed.

The nonoxidative catalytic n-butane dehydrogenation may be carried out in a tray reactor with or without oxygenous gas as a cofeed. It is preferably carried out with oxygenous gas as a cofeed. This reactor comprises one or more successive catalyst beds. The number of catalyst beds may be from 1 to 20, advantageously from 1 to 6, preferably from 1 to 4 and in particular from 1 to 3. The catalyst beds are preferably flowed through radially or axially by the reaction gas. In general, such a tray reactor is operated with a fixed catalyst bed. In the simplest case, the fixed catalyst beds are disposed axially in a shaft furnace reactor or in the annular gaps of concentric cylindrical grids. A shaft furnace reactor corresponds to one tray. The performance of the dehydrogenation in a single shaft furnace reactor corresponds to a preferred embodiment, in which it is possible to work with oxygenous cofeed. In a further preferred embodiment, the dehydrogenation is carried out in a tray reactor having 3 catalyst beds. In a method without oxygenous gas as cofeed, the reaction gas mixture is subjected to intermediate heating in the tray reactor on its way from one catalyst bed to the next catalyst bed, for example by passing it over heat exchanger plates heated by hot gases or by passing it through tubes heated by hot combustion gases.

In a preferred embodiment of the process according to the invention, the nonoxidative catalytic n-butane dehydrogenation is carried out autothermally. To this end, the reaction gas mixture of the n-butane dehydrogenation is additionally admixed with oxygen in at least one reaction zone and the hydrogen and/or hydrocarbon present in the reaction gas mixture is at least partially combusted, which generates directly in the reaction gas mixture at least a portion of the heat required for dehydrogenation in the at least one reaction zone.

In general, the amount of oxygenous gas added to the reaction gas mixture is selected in such a way that the amount of heat required for the dehydrogenation of n-butane is generated by the combustion of the hydrogen present in the reaction gas mixture and of any hydrocarbons present in the reaction gas mixture and/or of carbon present in the form of coke. In general, the total amount of oxygen supplied, based on the total amount of butane, is from 0.001 to 0.5 mol/mol, preferably from 0.005 to 0.2 mol/mol, more preferably from 0.05 to 0.2 mol/mol. Oxygen may be used either as pure oxygen or as an oxygenous gas in a mixture with inert gases, for example in the form of air. The inert gases and the resulting combustion gases generally have an additional diluting action and thus promote the heterogeneously catalyzed dehydrogenation.

The hydrogen combusted to generate heat is the hydrogen formed in the catalytic n-butane dehydrogenation and also any hydrogen additionally added to the reaction gas mixture as hydrogenous gas. The amount of hydrogen present should preferably be such that the molar $H_2/O_2$ ratio in the reaction gas mixture immediately after the oxygen has been fed in is from 1 to 10 mol/mol, preferably from 2 to 5 mol/mol. In multistage reactors, this applies to every intermediate feed of oxygenous and any hydrogenous gas.

The hydrogen is combusted catalytically. The dehydrogenation catalyst used generally also catalyzes the combustion of the hydrocarbons and of hydrogen with oxygen, so that in principle no specialized oxidation catalyst is required apart from it. One embodiment works in the presence of one or more oxidation catalysts which selectively catalyze the combustion of hydrogen with oxygen to water in the presence of hydrocarbons. The combustion of these hydrocarbons with oxygen to give CO, $CO_2$ and water therefore proceeds only to a minor extent. The dehydrogenation catalyst and the oxidation catalyst are preferably present in different reaction zones.

When the reaction is carried out in more than one stage, the oxidation catalyst may be present only in one or in more than one reaction zone, or in all reaction zones.

Preference is given to disposing the catalyst which selectively catalyzes the oxidation of hydrogen at the points where there are higher partial oxygen pressures than at other points in the reactor, in particular near the feed point for the oxygenous gas. The oxygenous gas and/or hydrogenous gas may be fed in at one or more points in the reactor.

In one embodiment of the process according to the invention, there is intermediate feeding of oxygenous gas and of hydrogenous gas upstream of every tray of a tray reactor. In a further embodiment of the process according to the invention, oxygenous gas and hydrogenous gas are fed in upstream of every tray except the first tray. In one embodiment, a layer of a specialized oxidation catalyst is present downstream of every feed point, followed by a layer of the dehydrogenation catalyst. In a further embodiment, no specialized oxidation catalyst is present. The dehydrogenation temperature is generally from 400 to 1100° C.; the pressure in the last catalyst bed of the tray reactor is generally from 0.2 to 5 bar, preferably from 1 to 3 bar. The GHSV is generally from 500 to 2000 $h^{-1}$, and in high-load operation, even up to 100 000 $h^{-1}$, preferably from 4000 to 16 000 $h^{-1}$.

A preferred catalyst which selectively catalyzes the combustion of hydrogen comprises oxides and/or phosphates selected from the group consisting of the oxides and/or phosphates or germanium, tin, lead, arsenic, antimony and bismuth. A further preferred catalyst which catalyzes the combustion of hydrogen comprises a noble metal of transition group VIII and/or I of the periodic table.

The dehydrogenation catalysts used generally comprise a support and an active composition. The support generally consists of a heat-resistant oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof, as a support. The mixtures may be physical mixtures or else chemical mixed phases such as magnesium aluminum oxide or zinc aluminum oxide mixed oxides. Preferred supports are zirconium dioxide and/or silicon dioxide, and particular preference is given to mixtures of zirconium dioxide and silicon dioxide.

The active compositions of the dehydrogenation catalysts generally comprise one or more elements of transition group VIII of the periodic table, preferably platinum and/or palladium, more preferably platinum. Furthermore, the dehydrogenation catalysts may comprise one or more elements of main group I and/or II, preferably potassium and/or cesium. The dehydrogenation catalysts may further comprise one or more elements of transition group III including the lanthanides and actinides, preferably lanthanum and/or cerium. Finally, the dehydrogenation catalysts may comprise one or more elements of main group III and/or IV, preferably one or more elements selected from the group consisting of boron, gallium, silicon, germanium, tin and lead, more preferably tin.

In a preferred embodiment, the dehydrogenation catalyst comprises at least one element of transition group VIII, at least one element of main group I and/or II, at least one element of main group III and/or IV and at least one element of transition group III including the lanthanides and actinides.

For example, all dehydrogenation catalysts which are disclosed in WO 99/46039, U.S. Pat. No. 4,788,371, EP-A 705 136, WO 99/29420, U.S. Pat. No. 5,220,091, U.S. Pat. No. 5,430,220, U.S. Pat. No. 5,877,369, EP 0 117 146, DE-A 199 37 106, DE-A 199 37 105 and DE-A 199 37 107 may be used in accordance with the invention. Particularly preferred catalysts for the above-described variants of the autothermal n-butane dehydrogenation are the catalysts according to examples 1, 2, 3 and 4 of DE-A 199 37 107.

Preference is given to carrying out the n-butane dehydrogenation in the presence of steam. The added steam serves as a heat carrier and supports the gasification of organic deposits on the catalysts, which counteracts carbonization of the catalysts and increases the lifetime of the catalysts. The organic deposits are converted to carbon monoxide, carbon dioxide and in some cases water.

The nonoxidative, catalytic n-butane dehydrogenation may also be operated with a cycle gas mode, which achieves higher conversions.

The dehydrogenation catalyst may be regenerated in a manner known per se. For instance, steam may be added to the reaction gas mixture or a gas comprising oxygen may be passed from time to time over the catalyst bed at elevated temperature and the deposited carbon burnt off. Dilution with steam shifts the equilibrium toward the products of dehydrogenation. After the regeneration, the catalyst is, if appropriate, reduced with a hydrogenous gas.

The nonoxidative catalytic n-butane dehydrogenation affords a gas mixture which, in addition to butadiene, 1-butene, 2-butene and unconverted n-butane, comprises secondary constituents, Customary secondary constituents are hydrogen, steam, nitrogen, CO and $CO_2$, methane, ethane, ethene, propane and propene. The composition of the gas mixture leaving the first dehydrogenation zone can vary greatly depending on the method of dehydrogenation. For instance, when the preferred autothermal dehydrogenation with feeding of oxygen and additional hydrogen is carried out, the product gas mixture comprises a comparatively high content of steam and carbon oxides. In methods without feeding of oxygen, the product gas mixture of the nonoxidative dehydrogenation has a comparatively high content of hydrogen.

The product gas stream of the nonoxidative autothermal n-butane dehydrogenation typically contains from 0.1 to 15% by volume of butadiene, from 1 to 15% by volume of 1-butene, from 1 to 25% by volume of 2-butene (cis/trans-2-butene), from 20 to 70% by volume of n-butane, from 1 to 70% by volume of steam, from 0 to 10% by volume of low-boiling hydrocarbons (methane, ethane, ethene, propane and propene), from 0.1 to 40% by volume of hydrogen, from 0 to 10% by volume of nitrogen and from 0 to 5% by volume of carbon oxides.

The product gas stream b leaving the first dehydrogenation zone can be separated into two substreams, in which case only one of the two substreams is subjected to the further process parts C to H and the second substream is recycled into the first dehydrogenation zone. An appropriate procedure is described in DE-A 102 11 275. However, it is also possible to subject the entire product gas stream b of the nonoxidative catalytic n-butane dehydrogenation to the further process parts C to H.

According to the invention, the nonoxidative catalytic dehydrogenation is followed downstream by an oxidative dehydrogenation (oxydehydrogenation) as process part C. This essentially dehydrogenates 1-butene and 2-butene to 1,3-butadiene, and 1-butene is generally virtually fully depleted.

This may in principle be carried out in all reactor types and methods known from the prior art, for example in a fluidized bed, in a tray furnace, in a fixed bed tubular or tube bundle reactor, or in a plate heat exchanger reactor. To carry out the oxidative dehydrogenation, a gas mixture is required which has a molar oxygen:n-butenes ratio of at least 0.5. Preference is given to working at an oxygen:n-butenes ratio of from 0.55 to 50. To attain this value, the product gas mixture stemming from the nonoxidative catalytic dehydrogenation is mixed with pure oxygen or an oxygenous gas. In the case of the first (autothermal) dehydrogenation stage B), the oxygenous gas comprises predominantly oxygen, at least 75% by volume, preferably at least 90% by volume, in order to minimize the inert gas fraction in the product gas stream of the oxydehydrogenation. Preference is given to oxygen of technical-grade purity. The resulting oxygenous gas mixture is then sent to the oxydehydrogenation.

The catalysts which are particularly suitable for the oxydehydrogenation are generally based on an Mo—Bi—O multimetal oxide system which generally additionally comprises iron. In general, the catalyst system also comprises additional components from groups 1 to 15 of the periodic table, for example potassium, magnesium, zirconium, chromium, nickel, cobalt, cadmium, tin, lead, germanium, lanthanum, manganese, tungsten, phosphorus, cerium, aluminum or silicon.

Suitable catalysts and their preparation are described, for example, in U.S. Pat. No. 4,423,281 ($Mo_{12}BiNi_8Pb_{0.5}Cr_3K_{0.2}O_x$ and, $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x+SiO_2$) and DE-A 24 40 329 ($Mo_{12}BiCo_{4.5}Ni_{2.5}Cr_3P_{0.5}K_{0.1}O_x$).

The stoichiometry of the active composition of a multitude of multimetal oxide catalysts suitable for the oxydehydrogenation can be encompassed under the general formula (I)

$$MO_{12}Bi_aFe_bCo_cNi_dCr_eX^1_fK_gO_x \quad (I)$$

in which the variables are each defined as fellows:

$X_1$=W, Sn, Mn, La, Ce, Ge, Ti, Zr, Hf, Nb, P, Si, Sb, Al, Cd and/or Mg;
a=from 0.5 to 5, preferably from 0.5 to 2;
b=from 0 to 5, preferably from 2 to 4;
c=from 0 to 10, preferably from 3 to 10;
d=from 0 to 10;
e=from 0 to 10, preferably from 0.1 to 4;
f=from 0 to 5, preferably from 0.1 to 2;
g=from 0 to 2, preferably from 0.0 1 to 1; and
x=a number which is determined by the valency and frequency of the elements in (I) other than oxygen.

In the process according to the invention, preference is given to using an Mo—Bi—Fe—O multimetal oxide system for the oxydehydrogenation, particular preference being given to an Mo—Bi—Fe—Cr—O or Mo—Bi—Fe—Zr—O multimetal oxide system. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x+SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$, $Mo_{12}BiFe_3Co_{4.5}Ni_{2.5}Mn_{0.5}K_{0.1}O_x$ and $Mo_{12}BiFe_3Co_{4.5}Ni_{2.5}La_{0.5}K_{0.1}O_z$), U.S. Pat. No. 3,911,039 ($Mo_{12}BiFe_3Co_{4.5}Ni_{2.5}Sn_{0.5}K_{0.1}O_x$), DE-A 25 30959 and DE-A 24 47 825 ($Mo_{12}BiFe_3Co_{4.5}Ni_{2.5}W_{0.5}K_{0.1}O_x$) The preparation and characterization of the catalysts mentioned are described comprehensively in the documents cited.

The oxydehydrogenation catalyst is generally used in the form of shaped bodies having an average size of over 2 mm. Owing to the pressure drop to be observed when the process is performed, smaller shaped bodies are generally unsuitable. Examples of suitable shaped bodies include tablets, cylinders, hollow cylinders, rings, spheres, strands, wagon wheels or extrudates. Special shapes, for example "trilobes" and "tristars" (see EP-A-0 593 646) or shaped bodies having at least one notch on the exterior (see U.S. Pat. No. 5,168,090) are likewise possible.

In general, the catalyst used may be used in the form of an unsupported catalyst. In this case, the entire shaped catalyst body consists of the active composition, including any auxiliaries, such as graphite or pore formers, and also further components. In particular, it has been found to be advantageous to use the Mo—Bi—Fe—O catalyst used with preference for the oxydehydrogenation of the n-butenes to butadiene in the form of an unsupported catalyst. Furthermore, it is possible to apply the active compositions of the catalysts to a support, for example an inorganic, oxidic shaped body. Such catalysts are generally referred to as coated catalysts.

The oxydehydrogenation is generally carried out at a temperature of from 220 to 490° C. and preferably from 250 to 450° C. A reactor inlet pressure is selected which is sufficient to overcome the flow resistances in the plant and the subsequent workup. This reactor inlet pressure is generally from 0.005 to 1 MPa gauge, preferably from 0.01 to 0.5 MPa gauge. By its nature, the gas pressure applied in the inlet region of the reactor decreases substantially over the entire catalyst bed.

The coupling of the nonoxidative catalytic, preferably autothermal, dehydrogenation with the oxidative dehydrogenation of the n-butenes formed affords a very much higher yield of butadiene based on n-butane used. The nonoxidative dehydrogenation can also be operated in a gentler manner. Comparable butadiene yields would only be achievable with an exclusively nonoxidative dehydrogenation at the cost of distinctly reduced selectivities. An exclusively oxidative dehydrogenation only achieves low n-butane conversions.

In addition to butadiene and unconverted n-butane, the product gas stream c leaving the oxidative dehydrogenation also comprises hydrogen, carbon dioxide and steam. As secondary constituents, it can also comprise oxygen, nitrogen, methane, ethane, ethene, propane and propene, and also oxygenous hydrocarbons, known as oxygenates. In general, it comprises virtually no 1-butene and only small fractions of 2-butene.

In general, the product gas stream c leaving the oxidative dehydrogenation has the following typical composition: from 10 to 40% by volume of butadiene, from 15 to 79.9% by volume of n-butane, from 0 to 10% by volume of 2-butene, from 0 to 2% by volume of 1-butene, from 10 to 70% by volume of steam, from 0 to 10% by volume of lowboiling hydrocarbons (methane, ethane, ethene, propane and propene), from 0.1 to 15% by volume of hydrogen, from 0 to 10% by volume of nitrogen, from 0 to 15% by volume of carbon dioxide and from 0 to 7% by volume of oxygenates. Oxygenates may, for example, be furan, acetic acid, maleic anhydride, maleic acid, propionic acid, acetaldehyde, acrolein, formaldehyde, formic acid and butyraldehyde. In addition, traces of acetylene, propyne and 1,2-butadiene may also be present.

The product gas stream c may also comprise small amounts of oxygen. When the product gas stream c contains more than just minor traces of oxygen, a catalytic combustion stage is preferably carried out in which oxygen is reacted with the hydrogen present in the gas stream c in the presence of a catalyst. This achieves a reduction in the oxygen content down to small traces.

A suitable catalyst for the oxidation of hydrogen comprises, supported on α-alumina, from 0.01 to 0.1% by weight of platinum and from 0.01 to 0.1% by weight of tin, based on the total weight of the catalyst. Platinum and tin are used advantageously in a weight ratio of from 1:4 to 1:0.2, preferably in a ratio of from 1:2 to 1:0.5, in particular in a ratio of approximately 1:1. Advantageously, the catalyst comprises from 0.05 to 0.09% by weight of platinum and from 0.05 to 0.09% by weight of tin, based on the total weight of the catalyst. In addition to platinum and tin, alkali metal and/or alkaline earth metal compounds may if appropriate be used in amounts of less than 2% by weight, in particular less than 0.5% by weight. More preferably, the alumina catalyst comprises exclusively platinum and tin. The catalyst support of α-alumina advantageously has a BET surface area of from 0.5 to 15 $m^2/g$, preferably from 2 to 14 $m^2/g$, in particular from 7 to 11 $m^2/g$. The support used is preferably a shaped body. Preferred geometries are, for example, tablets, annular tablets, spheres, cylinders, star extrudates or toothed wheel-shaped extrudates having diameters of from 1 to 10 mm, preferably from 2 to 6 mm. Particular preference is given to spheres or cylinders, in particular cylinders.

In one process stage, D), the gas stream c is compressed in at least one first compression stage and subsequently cooled, in the course of which at least one condensate stream d1 comprising water condenses out and the gas stream d2 comprising n-butane, butadiene, hydrogen, carbon dioxide and steam remains.

The compression may be effected in one or more stages. Overall, compression is generally effected from a pressure in the range from 1.0 to 4.0 bar (absolute) to a pressure in the range from 3.5 to 8.0 bar. Each compression stage is followed by a cooling stage in which the gas stream is cooled to a temperature in the range of generally from 15 to 60° C. The condensate stream d1 may thus also comprise a plurality of streams in the case of multistage compression.

The gas stream d2 consists generally substantially of $C_4$ hydrocarbons (substantially n-butane and butadiene), hydrogen, carbon dioxide and steam. The components mentioned generally make up a total of at least 80% by weight, preferably at least 90% by weight, of the gas stream d2. In addition, the stream d2 may also comprise low boilers, oxygen and inert gases (nitrogen) as further secondary components. The wastewater stream d1 consists generally to an extent of at least 80% by weight, preferably to an extent of at least 90% by weight, of water and comprises additionally, to a small extent, low boilers, $C_4$ hydrocarbons, oxygenates and carbon dioxide.

In one process stage, E), the gas stream d2 is compressed further in at least one further compression stage and subsequently cooled to condense out at least one condensate stream e1 comprising n-butane, butadiene and water and a gas stream e2 comprising n-butane, butadiene, hydrogen and carbon dioxide.

The compression may in turn be effected in one or more stages. In general, compression is effected overall from a pressure in the range from 3.5 to 8.0 bar to a pressure in the range from 12 to 40 bar. Each compression stage is followed by a cooling stage in which the gas stream is cooled to a temperature in the range of generally from 15 to 60° C. In the case of multistage compression, the condensate stream e1 may thus also comprise several streams.

The gas stream e2 consists generally substantially of $C_4$ hydrocarbons (substantially n-butane and butadiene), hydrogen and carbon dioxide, i.e. the components mentioned make up a total of at least 80% by weight, preferably at least 90% by weight, of the gas stream e2. In addition, it may also comprise small amounts of low boilers, oxygen and inert gases (nitrogen) as further secondary components. Steam may also be present in small amounts. The condensate stream e1 consists generally to an extent of at least 50% by weight, preferably to an extent of at least 80% by weight, of $C_4$ hydrocarbons (substantially n-butane and butadiene, with or without additional butene) and additionally also comprises water, low boilers, oxygenates and carbon dioxide.

Suitable compressors are, for example, turbo compressors and piston compressors including rotary piston compressors. The compressors may be driven, for example, by an electric motor, an expander or a gas or steam turbine. Typical compression ratios (outlet pressure:inlet pressure) for a compressor stage, depending on the design, are between 1.5 and 3.0.

The compressed gas is cooled by heat exchangers which may be designed, for example, as tube bundle, spiral or plate heat exchangers. The coolants used in the heat exchangers are cooling water or heat carrier oils. In addition, preference is given to using air cooling with use of fans.

In one process step, F), the gas stream e2 is cooled to obtain a condensate stream f1 comprising n-butane and butadiene and an offgas stream f2 comprising carbon dioxide and hydrogen. In general, the gas stream e2 is cooled to a temperature in the range from −30 to +20° C. The condensate stream f1 comprises predominantly $C_4$ hydrocarbons (substantially n-butane and butadiene), generally to an extent of at least 60% by weight, preferably to an extent of at least 70% by weight, and additionally also comprises carbon dioxide. In addition, it may also comprise low boilers and small amounts of water.

The condensate stream f1 may, for example, be condensed in surface condensers. In these condensers, the gas stream e2 comes into contact with tubes which are flowed through by cooling medium. Useful coolants are, for example, water, air and cooling brine. Injection condensers in which the coolant, preferably water, is injected directly into the gas stream which comprises the components to be condensed are also possible.

In one process step, G), water is removed by phase separation from the condensate stream(s) e1 and, if appropriate, the condensate stream f1 to obtain a $C_4$ hydrocarbon stream g1 comprising n-butane and butadiene and at least one wastewater stream g2.

To this end, the condensate streams are fed separately or combined to one or more phase separation apparatuses. One combined $C_4$ hydrocarbon stream g1 or a plurality of separate $C_4$ hydrocarbon streams g1 is/are obtained. The hydrocarbon stream(s) comprise predominantly $C_4$ hydrocarbons (substantially n-butane and butadiene), generally to an extent of at least 80% by weight, preferably to an extent of at least 85% by weight, and may additionally also comprise carbon dioxide and low boilers. The wastewater stream g2 comprises predominantly water, generally to an extent of at least 70% by weight, and additionally generally also comprises carbon dioxide. In addition, hydrocarbons (low boilers and $C_4$ hydrocarbons) may be present in small amounts, preferably up to a maximum of 1.0% by weight. The offgas stream g2 generally comprises predominantly carbon dioxide, additionally hydrogen, to a small extent $C_4$ hydrocarbons, with or without low boilers and inert gases (nitrogen).

To remove the hydrogen present in the offgas stream g2, it may, if appropriate after cooling, for example in an indirect heat exchanger, be passed through a membrane, generally configured as a tube, which is permeable only to molecular hydrogen. Alternatively, the hydrogen may also be removed by means of pressure swing absorption (PSA). The thus removed molecular hydrogen may, if required, be used at least partly in the dehydrogenation or else sent to another utilization, for example to generate electrical energy in fuel cells.

In one process step, H), the $C_4$ hydrocarbon stream g1 is separated into a recycle stream h1 comprising n-butane and a product stream h2 consisting substantially of butadiene, and the recycle stream h1 comprising n-butane is recycled into the first dehydrogenation zone.

The separation is preferably configured as an extractive distillation. The extractive distillation may be carried out, for example, as described in Erdöl und Kohle—Erdgas—Petrochemie [Mineral Oil and Coal Natural Gas—Petrochemistry] volume 34 (8), pages 343-346 or Ullmanns Enzyklopädie der Technischen Chemie, volume 9, 4th edition 1975, pages 1 to 18.

To this end, the $C_4$ product gas stream g1 is contacted in an extraction zone with an extractant, preferably an N-methylpyrrolidone (NMP)/water mixture. The extraction zone is generally configured in the form of a wash column which comprises trays, random packings or structured packings as internals. It generally has from 30 to 70 theoretical plates, so that sufficiently good separating action is achieved. The wash column preferably has a backwash zone in the top of the column. This backwash zone serves to recycle the extractant present in the gas phase by means of a liquid hydrocarbon reflux, for which the top fraction is condensed beforehand. Typical temperatures at the top of the column are between 30 and 60° C. The mass ratio of extractant to $C_4$ product gas stream g1 in the feed of the extraction zone is generally from 10:1 to 20:1.

Suitable extractants are butyrolactone, nitriles such as acetonitrile, propionitrile, methoxypropionitrile, ketones such as acetone, furfural, N-alkyl-substituted lower aliphatic amides such as dimethylformamide, diethylformamide, dimethylacetamide, diethylacetamide, N-formylmorpholine, N-alkyl-substituted cyclic amides (lactams) such as N-alkylpyrrolidones, especially N-methylpyrrolidone (NMP). In general, alkyl-substituted lower aliphatic amides or N-alkyl-substituted cyclic amides are used. Particularly advantageous are dimethylformamide, acetonitrile, furfural and especially NMP.

However, it is also possible to use mixtures of these extractants with one another, for example of NMP and acetonitrile, mixtures of these extractants with cosolvents and/or tert-butyl ethers, e.g. methyl tert-butyl ether, ethyl tert-butyl ether, propyl tert-butyl ether, n- or isobutyl tert-butyl ether. Particularly suitable is NMP, preferably in aqueous solution, preferably with from 0 to 20% by weight of water, more preferably with from 7 to 10% by weight of water, in particular with 8.3% by weight of water.

In the extractive distillation column, a gaseous strewn h1 consisting substantially of n-butane, which is generally drawn off via the top of the column, and an extraction solution comprising butadiene are formed. The side draw stream obtained is a mixture of extractant and butadiene. From this mixture, butadiene may be obtained subsequently as a pure product. The extractant which also comprises butadiene and any secondary components (impurities) is obtained as a side draw stream. The side draw stream is, if appropriate after carrying out further purification steps, recycled back into the extractive distillation.

For example, the extractive distillation, isolation of the pure butadiene and purification of the extractant may be carried out as follows: the side draw stream of the extractive distillation column, composed of extractant and butadiene which still comprises impurities (acetylene, propyne, 1,2-butadiene), is fed into a wash column which is charged with fresh extractant. At the top of the wash column, crude butadiene which comprises, for example, 98% by weight of butadiene is drawn off. The bottom draw stream is enriched with acetylene and is recycled into the extractive distillation. The crude butadiene may comprise propyne and 1,2-butadiene as impurities. To remove these impurities, the crude butadiene is fed to a first purifying distillation column and a propyne-enriched butadiene stream is removed overhead. The bottom draw stream which is substantially propyne-free, but still contains traces of 1,2-butadiene, is fed into a second purifying distillation column in which a substantially 1,2-butadiene-free pure butadiene stream having a purity of, for example, at least 99.6% by weight as a top draw stream or side draw stream in the rectifying section of the column, and a 1,2-butadiene-enriched bottom draw stream, are obtained.

To purify the extractant, a portion of the extractant is discharged from the extractive distillation column as a bottom draw stream and regenerated as follows: the extraction solution is transferred into a desorption zone with reduced pressure and/or elevated temperature compared to the extraction zone, and butadiene and acetylene traces present are desorbed from the extraction solution. The desorption zone may be designed, for example, in the form of a wash column which has from 5 to 15, preferably from 8 to 10, theoretical plates and a backwash zone having, for example, 4 theoretical plates. This backwash zone serves to recover the extractant present in the gas phase by means of liquid hydrocarbon recycling, for which the top fraction is condensed beforehand. The internals provided are structured packings, trays or random packings. The pressure added to the top of the column is, for example, 1.5 bar. The temperature in the bottom of the column is, for example, from 130 to 150° C. At the bottom of the column, a substantially acetylene-free extractant is obtained and is recycled into the extractive distillation column.

The product-of-value stream h2, as is obtained, for example, at the top draw stream of the second purifying distillation column, may comprise up to 100% by volume of butadiene.

The stream h1 consisting substantially of n-butane generally comprises at least 70% by weight of n-butane and additionally, as further constituents, also carbon dioxide, with or without butadiene, with or without butenes and low boilers.

EXAMPLE

By means of a simulation program, the process variant shown in the figure was simulated. A feed gas stream (4) comprising n-butane, said stream being obtained by combining a fresh gas stream (1) and a recycle stream (15), is fed to the first, autothermally operated, nonoxidative catalytic n-butane dehydrogenation stage (BDH) (16). To provide the heat required for the endothermic dehydrogenation, some of the hydrogen formed during the dehydrogenation is combusted selectively. To this end, combustion air is fed as stream (2). In order to counteract carbonization of the catalyst and prolong the lifetime of the catalyst, steam (3) is also added. A dehydrogenation gas mixture (5) is obtained, which is cooled after leaving the autothermal dehydrogenation stage (16) and fed to the second, oxidative, n-butane dehydrogenation stage (ODH) (17). Also fed to the ODH (17) is an oxygen stream (6). For BDH and ODH, based on experimental results, the degrees of conversion and selectivities reproduced in Table 1 were assumed.

TABLE 1

| Reaction stage | Conversion [%] | Selectivity [%] |
| --- | --- | --- |
| Autothermal dehydrogenation (BDH) | 49.5 (n-butane) | 97.9 (to butenes/butadiene) |
| Oxidative dehydrogenation (ODH) | 100.0 (1-butene) 92.7 (2-butene) | 95.0 (to butadiene) |

The exit gas of the oxydehydrogenation (7), which is under a pressure of 2.4 bar (absolute), is compressed to a pressure of 30.1 bar in a plurality of compressors (18) in a plurality of stages with intermediate cooling, and the compressed gas (9) is cooled to a temperature of 5° C. in a condenser (19). The uncondensed offgas (10) is hydrogen-rich and is sent either to an incineration or to a material utilization (pressure swing absorption, membrane separation of the hydrogen). The condensate (8) which is obtained after the second compressor stage and intermediate cooling at a pressure of 12 bar and a temperature of 55° C. and the condensate (11) which is obtained after the third compressor stage at the end pressure of 30.1 bar and the temperature of 5° C. are separated in a phase separator (20) into an aqueous phase (wastewater stream 13) and an organic phase (12). The condensate (13b) which is obtained after the first compressor stage and intermediate cooling at a pressure of 5 bar and a temperature of 55° C. may be sent directly to the wastewater. Finally, a butadiene extraction is effected in an extractive distillation using NMP as a solvent and removing the butadiene (14). (21) here designates the entirety of extraction column, wash column and butadiene purifying distillation columns (21). The n-butane-rich stream (15) remaining after the butadiene extraction is combined with the fresh n-butane feed gas stream (1) and recycled into the first dehydrogenation stage.

The results of the simulation calculation are reported in Table 2. The composition of the streams (1) to (15) is reported in parts by weight.

TABLE 2

| | Stream No. | | | | | | | |
| --- | --- | --- | --- | --- | --- | --- | --- | --- |
| | 1 | 2 | 3 | 4 | 5 | 6 | 7 | 8 |
| Amount [kg/h] | 25,143 | 4,838 | 1,250 | 61,001 | 61,001 | 10,016 | 71,016 | 33,867 |
| PROPANE | 0.0000 | 0.0000 | 0.0000 | 0.0264 | 0.0329 | 0.0000 | 0.0282 | 0.0319 |
| BUTANE | 1.0000 | 0.0000 | 0.0000 | 0.8265 | 0.4176 | 0.0000 | 0.3587 | 0.5177 |
| 1-BUTENE | 0.0000 | 0.0000 | 0.0000 | 0.0000 | 0.1142 | 0.0000 | 0.0000 | 0.0000 |
| CIS-2-BUTENE | 0.0000 | 0.0000 | 0.0000 | 0.0034 | 0.1162 | 0.0000 | 0.0050 | 0.0046 |
| TRANS-2-BUTENE | 0.0000 | 0.0000 | 0.0000 | 0.0077 | 0.1455 | 0.0000 | 0.0112 | 0.0105 |
| 1,3-BUTADIENE | 0.0000 | 0.0000 | 0.0000 | 0.0000 | 0.0209 | 0.0000 | 0.2989 | 0.4013 |
| WATER | 0.0000 | 0.0000 | 1.0000 | 0.0217 | 0.1052 | 0.0000 | 0.2036 | 0.0159 |
| CARBON DIOXIDE | 0.0000 | 0.0000 | 0.0000 | 0.0342 | 0.0407 | 0.0000 | 0.0831 | 0.0182 |
| HYDROGEN | 0.0000 | 0.0000 | 0.0000 | 0.0000 | 0.0056 | 0.0000 | 0.0048 | 0.0000 |
| OXYGEN | 0.0000 | 1.0000 | 0.0000 | 0.0793 | 0.0004 | 0.9912 | 0.0045 | 0.0000 |
| N2 | 0.0000 | 0.00 | 0.0000 | 0.0008 | 0.0008 | 0.0088 | 0.0019 | 0.0000 |
| Temperature [° C.] | 25 | 180 | 144 | 420 | 520 | 143 | 380 | 55 |
| Pressure [bar] | 5 | 4.00 | 4.00 | 3.20 | 2.70 | 2.70 | 2.40 | 12 |
| | Stream No. | | | | | | | |
| | 9 | 10 | 11 | 12 | 13 | 13b | 14 | 15 |
| Amount [kg/h] | 22,086 | 4,524 | 17,562 | 50,688 | 741 | 15,063 | 20,750 | 29,728 |
| PROPANE | 0.0284 | 0.0127 | 0.0324 | 0.0317 | 0.0543 | 0.0199 | 0.0000 | 0.0541 |
| BUTANE | 0.3596 | 0.0420 | 0.4415 | 0.4988 | 0.0016 | 0.0001 | 0.0000 | 0.8505 |
| 1-BUTENE | 0.0000 | 0.0000 | 0.0000 | 0.0000 | 0.0000 | 0.0000 | 0.0000 | 0.0000 |
| CIS-2-BUTENE | 0.0026 | 0.0002 | 0.0032 | 0.0040 | 0.0107 | 0.0093 | 0.0000 | 0.0069 |
| TRANS-2-BUTENE | 0.0061 | 0.0005 | 0.0076 | 0.0093 | 0.0239 | 0.0199 | 0.0000 | 0.0159 |
| 1,3-BUTADIENE | 0.3455 | 0.0570 | 0.4198 | 0.4135 | 0.0030 | 0.0003 | 1.0000 | 0.0000 |
| WATER | 0.0058 | 0.0001 | 0.0073 | 0.0014 | 0.8018 | 0.9397 | 0.0000 | 0.0025 |
| CARBON DIOXIDE | 0.2319 | 0.7900 | 0.0882 | 0.0412 | 0.1046 | 0.0108 | 0.0000 | 0.0702 |
| HYDROGEN | 0.0137 | 0.0668 | 0.0000 | 0.0000 | 0.0000 | 0.0000 | 0.0000 | 0.0000 |
| OXYGEN | 0.0001 | 0.0007 | 0.0000 | 0.0000 | 0.0000 | 0.0000 | 0.0000 | 0.0000 |
| N2 | 0.0062 | 0.0301 | 0.0000 | 0.0000 | 0.0000 | 0.0000 | 0.0000 | 0.0000 |
| Temperature [° C.] | 101 | 5 | 5 | 30 | 30 | 55 | 114 | 114 |
| Pressure [bar] | 30.1 | 30.1 | 30.1 | 25 | 25 | 5 | 5 | 5 |

What is claimed is:

1. A process comprising:

(a) providing a feed gas stream comprising n-butane;

(b) non-oxidatively dehydrogenating the feed gas stream in the presence of a catalyst in a first dehydrogenation zone to form a first intermediate gas stream comprising n-butane, 1-butene, 2-butene, butadiene and hydrogen;

(c) oxidatively dehydrogenating the first intermediate gas stream in the presence of an oxygenous gas having an oxygen content of at least 75% by volume in a second dehydrogenation zone to form a second intermediate gas stream comprising n-butane, butadiene, hydrogen, carbon dioxide and steam;

(d) compressing and cooling the second intermediate gas to form a first condensate stream comprising water and a third intermediate gas stream comprising n-butane, butadiene, hydrogen, carbon dioxide and steam;

(e) compressing and cooling the third intermediate gas to form a second condensate stream comprising n-butane, butadiene and water and a fourth intermediate gas stream comprising n-butane, butadiene, hydrogen and carbon dioxide;

(f) cooling the fourth intermediate gas stream to form a third condensate stream comprising n-butane and butadiene, and an offgas stream comprising carbon dioxide and hydrogen;

(g) removing water from the second condensate stream and combining the second condensate stream and third condensate stream to form a $C_4$ hydrocarbon stream comprising n-butane and butadiene; and (h) separating the $C_4$ hydrocarbon stream to form a recylce stream comprising n-butane and a product stream comprising butadiene;

wherein at least a portion of the recycle stream is fed to the first dehydrogenation zone.

2. The process according to claim 1, wherein removing water from the second condensate stream is carried out prior to combining the second condensate stream and third condensate stream.

3. The process according to claim 1, wherein the non-oxidative dehydrogenation in the first dehydrogenation zone is carried out autothermally in the presence of an oxygenous gas having an oxygen content of at least 90% by volume.

4. The process according to claim 3, wherein the oxygenous gas comprises technical grade oxygen.

5. The process according to claim 1, wherein the feed gas stream is obtained from liquefied petroleum gas.

6. The process according to claim 1, wherein providing the feed gas stream comprises:

(i) providing a liquefied petroleum gas stream comprising butane and non-butyl hydrocarbons;

(ii) removing at least a portion of the non-butyl hydrocarbons from the liquefied petroleum gas stream to form an initial stream comprising n-butane and isobutane; and (iii) removing at least a portion of the isobutane from the initial stream to form the feed gas stream.

7. The process according to claim 6, further comprising isomerizing the isobutane removed from the initial stream to form an n-butane/isobutane mixture and recycling the n-butane/isobutane mixture into the initial stream.

8. The process according to claim 6, wherein the non-oxidative dehydrogenation in the first dehydrogenation zone is carded out autothermally in the presence of an oxygenous gas having an oxygen content of at least 90% by volume.

9. The process according to claim 1, wherein the oxygenous gas comprises technical grade oxygen.

10. The process according to claim 1, wherein separating the $C_4$ hydrocarbon stream comprises extractive distillation.

11. The process according to claim 6, wherein separating the $C_4$ hydrocarbon stream comprises extractive distillation.

12. The process according to claim 9, wherein separating the $C_4$ hydrocarbon stream comprises extractive distillation.

13. The process according to claim 1, wherein the second intermediate gas stream further comprises residual oxygen, and the process further comprises removing at least a portion of the residual oxygen from the second intermediate gas stream prior to compressing and cooling the second intermediate gas stream.

* * * * *